United States Patent
Ruan et al.

(10) Patent No.: US 9,943,470 B2
(45) Date of Patent: Apr. 17, 2018

(54) LIQUID SKIN CLEANSER

(71) Applicant: Colgate-Palmolive Company, New York, NY (US)

(72) Inventors: Yang Ruan, Guangzhou (CN); Huiyan Yin, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/533,380

(22) PCT Filed: Dec. 18, 2014

(86) PCT No.: PCT/CN2014/094170
§ 371 (c)(1),
(2) Date: Jun. 6, 2017

(87) PCT Pub. No.: WO2016/095145
PCT Pub. Date: Jun. 23, 2016

(65) Prior Publication Data
US 2018/0021232 A1    Jan. 25, 2018

(51) Int. Cl.
| | | |
|---|---|---|
| *A61K 8/36* | (2006.01) | |
| *A61Q 19/10* | (2006.01) | |
| *A61K 8/04* | (2006.01) | |
| *A61K 8/46* | (2006.01) | |
| *A61K 8/45* | (2006.01) | |
| *A61K 8/44* | (2006.01) | |

(52) U.S. Cl.
CPC .............. *A61K 8/361* (2013.01); *A61K 8/046* (2013.01); *A61K 8/442* (2013.01); *A61K 8/45* (2013.01); *A61K 8/463* (2013.01); *A61Q 19/10* (2013.01); *A61K 2800/51* (2013.01); *A61K 2800/524* (2013.01); *A61K 2800/74* (2013.01)

(58) Field of Classification Search
None
See application file for complete search history.

(56) References Cited

U.S. PATENT DOCUMENTS

| | | |
|---|---|---|
| 8,778,861 B2 | 7/2014 | Shi et al. |
| 2007/0066500 A1 | 3/2007 | Yang et al. |

FOREIGN PATENT DOCUMENTS

| | | |
|---|---|---|
| WO | WO2006/087086 | 8/2006 |
| WO | WO2012/041591 | 4/2012 |

OTHER PUBLICATIONS

AMOREPACIFIC, 2012, "Olive Hand Wash," Mintel GNPD AN: 1763044.
International Search Report and Written Opinion of the International Searching Authority in International Application No. PCT/CN2014/094170, dated Sep. 30, 2015.
Kanebo Cosmetics, 2002, "Perfect Water Soap," Mintel GNPD AN: 152098.
Sheng-Hsiang-Tang Chemical Industrial, 2010, "Antibacterial Hand Wash," Mintel GNPD AN: 1387219.

*Primary Examiner* — Necholus Ogden, Jr.

(57) ABSTRACT

A skin cleansing composition comprising a salt of lauric acid; a salt of stearic acid; and at least one surfactant that is not a salt of a fatty acid; wherein the ratio of the salt of lauric acid to the salt of stearic acid, calculated as the ratio of lauric acid to stearic acid by weight, is from 2.5:1 to 3.5:1. Also provided are methods of using the compositions.

14 Claims, No Drawings

LIQUID SKIN CLEANSER

BACKGROUND

Liquid skin cleansers have become very popular with consumers over the last twenty years. It is desirable for such skin cleansers to rinse of easily, and also leave the skin with a "squeaky-clean" feel. Consequently, there is a need for liquid skin cleansing compositions that are effective cleansers, and also leave the skin feeling clean.

BRIEF SUMMARY

The inventors have discovered that the combination of a salt of a short chain fatty acid, for example lauric acid, together with a blend of salts of long chain fatty acids, for example a blend of palmitic and stearic acid, provides excellent sensory and performance properties when formulated into a skin cleansing composition. Preferably, the ratio of the amount of short chain faty acid, to the amount of blend of long chain fatty acid is from 2.5:1 to 3.5:1. The compositions also possess superior antibacterial efficacy, allowing for use of a lower dosage of antibacterial compound in the composition.

In a first exemplary embodiment, the present disclosure provides a liquid skin cleanser composition comprising:
a) a salt of lauric acid;
b) a blend of salts of stearic acid and palmitic acid; and
c) at least one surfactant that is not a salt of a fatty acid;
wherein the ratio of the salt of lauric acid to the blend of salts of stearic acid and palmitic acid, calculated as the ratio by weight of lauric acid to combined weight of stearic acid and palmitic acid, is from 2.5:1 to 3.5:1. Optionally, the liquid skin cleanser contains an antibacterial agent.

In further exemplary embodiments, the disclosure provides methods of cleaning skin using the disclosed compositions, and methods for their preparation.

DETAILED DESCRIPTION

Unless otherwise specified, all percentages and amounts expressed herein and elsewhere in the specification should be understood to refer to percentages by weight. As used throughout, ranges are used as shorthand for describing each and every value that is within the range. Any value within the range can be selected as the terminus of the range.

As used herein, the term "liquid skin cleaning composition" shall include non-solid forms such as creams and gels, for cleansing and personal hygienic use comprising at least one cleanser chosen from soap and surfactant.

In one exemplary embodiment, the present disclosure provides a liquid skin cleanser composition (Composition 1) comprising:
a) a salt of lauric acid; and
b) a blend of salts of stearic acid and palmitic acid; and
c) at least one surfactant that is not a salt of a fatty acid;
wherein the ratio of the salt of lauric acid to the blend of salts of stearic acid and palmitic acid, calculated as the ratio by weight of lauric acid to combined weight of stearic acid and palmitic acid, is from 2.5:1 to 3.5:1; for example:

1.1 Composition 1, wherein the ratio of the salt of lauric acid to the combined salts of palmitic and stearic acids, calculated as the ratio of weight of lauric acid to combined weight of palmitic and stearic acid, is about 3:1.

1.2 Composition 1 or 1.1, wherein the ratio of the amount of salt of palmitic acid to the amount of salt of stearic acid in the blend, calculated as the ratio of weight of palmitic acid to stearic acid in the blend is from 1.3:1 to 1.8:1; preferably about 1.5:1.

1.3 Any preceding Composition 1 et seq., wherein the salts of lauric acid, stearic acid and palmitic acid are alkali metal (e.g., sodium or potassium) salts, triethanolamine salts, ammonium salts, and combinations thereof.

1.4 Any preceding Composition 1 et seq., wherein the salts of lauric acid, stearic acid and palmitic acid are potassium salts.

1.5 Any preceding Composition 1 et seq., which is devoid of myristic acid or its salts.

1.6 Any preceding Composition 1 et seq., which is devoid of salts of fatty acids other than the salts of lauric acid, stearic acid and palmitic acid.

1.7 Any preceding Composition 1 et seq. further comprising an antibacterial agent.

1.8 Composition 1.6, wherein the antibacterial agent is trichlorocarbanilide, in an amount of from 0.01% to 0.15% by weight of the composition, for example from 0.1% to 0.15% by weight of the composition.

1.9 Composition 1.6 or 1.7, wherein the antibacterial agent is trichlorocarbanilide, which is present in an amount of from 0.01% to 0.3% by weight of the composition.

1.10 Any preceding Composition 1 et seq., wherein the at least one surfactant that is not a salt of a fatty acid is selected from anionic surfactants, amphoteric surfactants, zwitterionic surfactants, and non-ionic surfactants.

1.11 Any preceding Composition 1 et seq., wherein the at least one surfactant that is not a salt of a fatty acid is selected from the group consisting of sodium or ammonium salts of alkyl ether sulfates, sodium laureth sulfate, and combinations thereof.

1.12 Any preceding Composition 1 et seq., wherein the at least one surfactant that is not a salt of a fatty acid is sodium laureth sulfate, which is present in the composition an amount of from 5% to 12% by weight; for example about 8% by weight.

1.13 Any preceding Composition 1 et seq., wherein the at least one surfactant that is not a salt of a fatty acid is an ethoxylated fatty alcohol.

1.14 Any preceding Composition 1 et seq., wherein the ethoxylated fatty alcohol is present in the composition an amount of from 0.2% to 1% by weight; optionally about 0.6% by weight.

1.15 Any preceding Composition 1 et seq., wherein the at least one surfactant that is not a salt of a fatty acid is a propoxylated monoethanolamide.

1.16 Composition 1.14, wherein the propoxylated monoethanolamide is PPG-2 Hydroxyethyl Cocamide, which is present in the composition an amount of from 0.2% to 1% by weight; optionally about 0.6% by weight.

1.17 Any preceding Composition 1 et seq., wherein the at least one surfactant that is not a salt of a fatty acid is cocoamidopropyl betaine.

1.18 Composition 1.16, wherein the cocoamidopropyl betaine is present in an amount of 5% to 12% of the composition by weight, optionally 8% to 9% of the composition by weight.

1.19 Any preceding Composition 1 et seq., further comprising cocomonoethanolamide in an amount of from 0.5% to 2.5% of the composition by weight, for example about 1.5% of the composition by weight.

1.20 Any preceding Composition 1 et seq., wherein the composition comprises
  a) potassium laurate,
  b) potassium stearate,
  c) potassium palmitate,
  d) sodium laureth sulfate,
  e) cocoamidopropyl betaine,
  f) ethoxylated fatty alcohol, and
  g) cocomonoethanolamide.
1.21 Any preceding Composition 1 et seq., wherein the composition comprises:
  a) 4 to 6% by weight of the potassium laurate,
  b) 1 to 2% by weight of the potassium stearate,
  c) 0.8 to 2% by weight of the potassium palmitate,
  d) 8 to 13% by weight of the sodium laureth sulfate,
  e) 5 to 9% by weight of the cocoamidopropyl betaine,
  f) 0.6 to 1.2% by weight of the ethoxylated fatty alcohol, and
  g) 0.5 to 2% by weight of the cocomonoethanolamide.

The liquid skin cleanser compositions of the invention comprise a metal salt of lauric acid, and metal salts of a blend of palmitic and stearic acids. Preferably, the metal salts are alkali metal salts, e.g., sodium or potassium salts. In some preferred embodiments, the salts are potassium salts.

The inventors have discovered that the combination of a salt of a short chain fatty acid, for example lauric acid, together with a blend of salts of long chain fatty acids, for example a blend of palmitic and stearic acid, provides excellent sensory and performance properties when formulated into a skin cleansing composition. Preferably, the compositions comprise a ratio of the amount of short chain fatty acid, to the amount of blend of long chain fatty acid, of from 2.5:1 to 3.5:1, calculated as the weight of the acid. The blend of long chain fatty acids contains, in some preferred embodiments, a ratio of amount of palmitic acid to amount of stearic acid by weight of from 1.3:1 to 1.8:1; preferably about 1.5:1. For example, in some preferred embodiments, the compositions of the invention comprise a blend of 40% by weight stearic acid and 60% by weight palmitic acid, together with an amount of lauric acid, such that the ratio of the weights of lauric acid relative to combined weights of palmitic and stearic acid, is from 2.5:1 to 3.5:1, preferably about 3:1.

The compositions also possess superior antibacterial efficacy, allowing for use of a lower dosage of antibacterial compound in the composition.

While not wishing to be bound by particular theory, it is believed that differences in carbon chains of fatty acid soaps affect attributes like skin feel, ease of rinse off, lathering, and formula thickening properties. In particular, Applicants have discovered that that long chain fatty acid soaps, for example those having eighteen or carbon atoms, are key contributors to producing a squeaky skin feel, which is attractive to many consumers. Thus, in some embodiments, the compositions do not contain myristic, or its salts. In some embodiments, the compositions are devoid of salts of fatty acids other than the salts of lauryl acid, palmitic acid and stearic acid.

The lauric acid and palmitic/stearic acid salts can be added directly to the formulation, or they can be created in situ from their parent acids. For example, the desired amount of lauric acid and blend of palmitic and stearic acids can be added to the formulation, and the pH adjusted, for example by addition of an aqueous hydroxide such as potassium hydroxide, to form the solubilized salts. Thus, as used herein, the ratio of the salt of lauric acid to the salts of stearic acid and palmitic acid, calculated as the ratio of lauric acid to palmitic and stearic acid by weight, is intended to mean the relative amounts of salts of lauric acid, palmitic acid and stearic acid produced by adding the indicated ratio of the corresponding acids.

The compositions optionally contain an antibacterial agent. Suitable antibacterial agents for the compositions of the invention include, but are not limited to, trichlorocarbanilide, triclocarban, PCMX/chloroxylenol, IPMP/o-Cymen-5-ol, Zinc Compounds, and Phenoxyethanol. Typically, the antibacterial agent is present in an amount of from 0.01% to 0.75%, for example from 0.01% to 0.3 by weight of the composition. In some preferred embodiments, the compositions include trichlorocarbanilide in an amount of from 0.01% to 0.3% by weight of the composition, preferably about 0.1% by weight of the composition.

The compositions disclosed herein also contain, in addition to the aforementioned lauric, palmitic and stearic acid salts, at least one surfactant that is not a fatty acid or a salt of a fatty acid. In certain embodiments, the surfactant is at least one of an anionic surfactant, an amphoteric surfactant, a zwitterionic surfactant, and a non-ionic surfactant. In some embodiments, the surfactant is an anionic surfactant, for example a sulfate, sulfonate alpha olefin sulfonate, isethionate such as SCI, N-alkyl or N-acyl taurate, sulfosuccinate, or phosphate. In some embodiments, the surfactant is sodium laureth sulfate (SLES), preferably in an amount of from 5% to 12% of the composition by weight, for example about 8% of the composition by weight.

The compositions disclosed herein can also contain one or more nonionic surfactants, for example and not limited to propoxylated monoethanolamides such as PPG-2 Hydroxyethyl Cocamide (Promidium CO), alkanolamides, alkylpolyglycosides which each can be present in the composition in an amount of from 0.2% to 1% by weight; for example about 0.6% by weight.

In some embodiments, the compositions comprise cocoamidopropyl betaine in an amount of from 5% to 12% of the composition by weight, for example from 8% to 9% of the composition by weight.

In some embodiments, the compositions comprise cocomonoethanolamide in an amount of from 0.5% to 2.5% of the composition by weight, for example about 1.5% of the composition by weight. In some embodiments, the compositions comprise both cocoamidopropyl betaine and cocomonoethanolamide in the amounts stated above.

The compositions disclosed herein can also contain one or more preservatives, for example and not limited to isothiazolinones such as methylchloroisothiazolinone, alone or in combination with methylisothiazolinone (e.g., Kathon™ CG), parabens (such as propylparaben, ethylparaben and methylparaben), benzalkonium chloride, 2-bromo-2-nitropropane-1,3-diol, Germaben H, a product of Sutton Laboratories, Inc., which comprises propylene glycol 50%, diazolidinyl urea 30%, methylparaben 11%, and propylparaben 3%, hydantoins, imidazolines and BHT.

The compositions disclosed herein can also contain one or more chelating agents, which can possess both preservative and antibacterial functionality, sequestering metals that bacteria require in order to grow. Suitable chelating agents include tetrasodium EDTA, pentetic acid, and pentasodium pentetate. One preferred chelating agent is tetrasodium EDTA.

The compositions disclosed herein can also contain one or more alpha hydroxy acids, for example citric acid. Such alpha hydroxy acids are known to be useful for adjust the pH balance of the composition, and also for promoting skin peeling and re-growth.

The compositions of this invention also may contain minor amounts of conventional additional components, to impart any desired characteristic, which are compatible with the skin cleanser formulation, and do not adversely affect its properties. Suitable additives include, but are not limited to, fragrances, colorants, skin conditioning agents, moisturizing agents, dyes and pigments, titanium dioxide, sunscreen active ingredients such as butyl methoxy benzoylmethane; antiaging compounds such as alpha hydroxy acids, beta hydroxy acids; polyols such as glycerol, sorbitol, propylene glycol and polyethylene glycols; particulate matter such as silica, talc, or calcium carbonate; antioxidants such as butylated hydroxytoluene (BHT); vitamins such as A, E, K and C; essential oils and extracts thereof such as rosewood and jojoba, particulate matter such as polyethylene beads, jojoba beads, lufa, or oat flour, and mixtures of any of the foregoing components.

It will be recognized that individual components of the disclosed compositions may possess multiple functionalities.

In a further embodiment, the present disclosure also provides a method of cleaning skin comprising contacting the skin with any of Compositions 1-1.20.

In a further embodiment, use of a metal salt of lauric acid and a blend of metal salts of palmitic acid and stearic acid in a liquid skin cleanser that contains at least one surfactant that is not a salt of a fatty acid for providing a squeaky clean feeling on skin after cleansing (Use 1).

1.1 Use 1, wherein the liquid skin cleanser is devoid of myristic acid or its salts.
1.2 Use 1 or 1.1, wherein the liquid skin cleanser is devoid of salts of fatty acids other than the metal salts of lauric acid, palmitic acid and stearic acid.

The liquid skin cleanser composition of the present disclosure may be prepared by any of the techniques known to those skilled in the art, including both batch processes and continuous processes.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997).

Example 1

Table 1 shows the composition of a formulation according to the invention and a comparative formulation containing myristic acid and a fatty acid blend.

TABLE 1

Exemplary Composition of the Invention

| Ingredient | Comparative Weight % | Inventive Weight % |
|---|---|---|
| Demineralized Water and minors (antibacterial agent, preservative, pH adjustment, fragrance, etc.) | Q.S. | Q.S. |
| SLES 70% | 8 | 8 |
| Cocoamidopropyl Betaine | 8.45 | 8.45 |
| Cocomonoethanolamide | 0 | 1.5 |
| 47% Potassium Hydroxide soln. | 4.2 | 4 |
| Lauric Acid | 4.3 | 5.5 |
| C12-18 Fatty acid blend | 2.1 | 0 |
| Myristic Acid | 1.7 | 0 |
| Blend of 40 wt. % Stearic Acid and 60 wt. % Palmitic Acid | 0 | 1.8 |
| Ethoxylated alcohol | 0.9 | 0.6 |
| PPG-2 Hydroxyethyl Cocamide | 0.9 | 0.6 |
| Potassium chloride | 2 | 1.3 |

The compositions were used by panelists and rated on a scale of 1 to 10 for squeaky clean feel. The compositions had parity performance, but the inventive composition had a lower cost based on the combination of the lauric acid and stearic acid salts.

Example 2

Foam Profile

An in-vitro laboratory foam profile was conducted. The results showed that the inventive composition of Table 1 had significant improvement observed in foam generation relative to the comparative formulation due to the balance of fatty acids ratio. The results are in Table 2 below.

| Time (s) | Comparative Volume (ml) | Inventive Formulation Volume (ml) |
|---|---|---|
| 0 | 0 | 0 |
| 10 | 117 | 141 |
| 20 | 173 | 211 |
| 30 | 220 | 274 |
| 40 | 259 | 316 |
| 50 | 287 | 346 |
| 60 | 303 | 367 |
| 70 | 315 | 389 |
| 80 | 324 | 411 |
| 90 | 339 | 427 |
| 100 | 348 | 446 |

What is claimed is:
1. A liquid skin cleanser composition comprising:
a salt of lauric acid;
a blend of salts of stearic acid and palmitic acid;
at least one surfactant that is not a salt of a fatty acid; and
cocomonoethanolamide;
wherein the ratio of the salt of lauric acid to the blend of salts of stearic acid and palmitic acid, calculated as the ratio by weight of lauric acid to combined weight of stearic acid and palmitic acid, is from 2.5:1 to 3.5:1;
wherein the salt of lauric acid is potassium laurate; the blend of salts of stearic acid and palmitic acid is a blend of potassium stearate and potassium palmitate; the at least one surfactant that is not a salt of a fatty acid includes sodium laureth sulfate, cocoamidopropyl betaine, and ethoxylated fatty alcohol.

2. The composition of claim 1, wherein the ratio of the salt of lauric acid to the combined salts of palmitic and stearic acids, calculated as the ratio of weight of lauric acid to combined weight of palmitic and stearic acid, is about 3:1.

3. The composition of claim 1, wherein the ratio of the amount of salt of palmitic acid to the amount of salt of stearic acid in the blend, calculated as the ratio of weight of palmitic acid to stearic acid in the blend is from 1.3:1 to 1.8:1; preferably about 1.5:1.

4. The composition of claim 1, which is devoid of myristic acid, or its salts.

5. The composition of claim 1, which is devoid of salts of fatty acids other than the salts of lauric acid, palmitic acid and stearic acid.

6. The composition of claim 1 further comprising an antibacterial agent.

7. The composition of claim 6, wherein the antibacterial agent is selected from trichlorocarbanilide, triclocarban, PCMX/chloroxylenol, IPMP/o-Cymen-5-ol, Zinc Compounds, and Phenoxyethanol, wherein the antibacterial agent is present in an amount of from 0.01% to 3% by weight of the composition.

8. The composition of claim 6, wherein the antibacterial agent is trichlorocarbanilide, which is present in an amount of from 0.01% to 0.3% by weight of the composition.

9. The composition of claim 1, wherein sodium laureth sulfate is present in the composition an amount of from 5% to 12% by weight.

10. The composition of claim 1, wherein the ethoxylated fatty alcohol is present in the composition an amount of from 0.2% to 1% by weight.

11. The composition of claim 1, wherein the at least one surfactant that is not a salt of a fatty acid further comprises a propoxylated monoethanolamide, wherein the propoxylated monoethanolamide is PPG-2 Hydroxyethyl Cocamide, which is present in the composition an amount of from 0.2% to 1% by weight.

12. The composition of claim 1, wherein the cocoamidopropyl betaine is present in an amount of 5% to 12% of the composition by weight.

13. The composition of claim 1, wherein cocomonoethanolamide is present in an amount of from 0.5% to 2.5% of the composition by weight.

14. The composition of claim 1, wherein the composition comprises:
 4 to 6% by weight of the potassium laurate,
 1 to 2% by weight of the potassium stearate,
 0.8 to 2% by weight of the potassium palmitate,
 8 to 13% by weight of the sodium laureth sulfate,
 5 to 9% by weight of the cocoamidopropyl betaine,
 0.6 to 1.2% by weight of the ethoxylated fatty alcohol, and
 0.5 to 2% by weight of the cocomonoethanolamide.

* * * * *